Jan. 22, 1974 H. BRANDKAMP ETAL Plant Pat. 3,449
CHRYSANTHEMUM PLANT
Filed Jan. 17, 1972
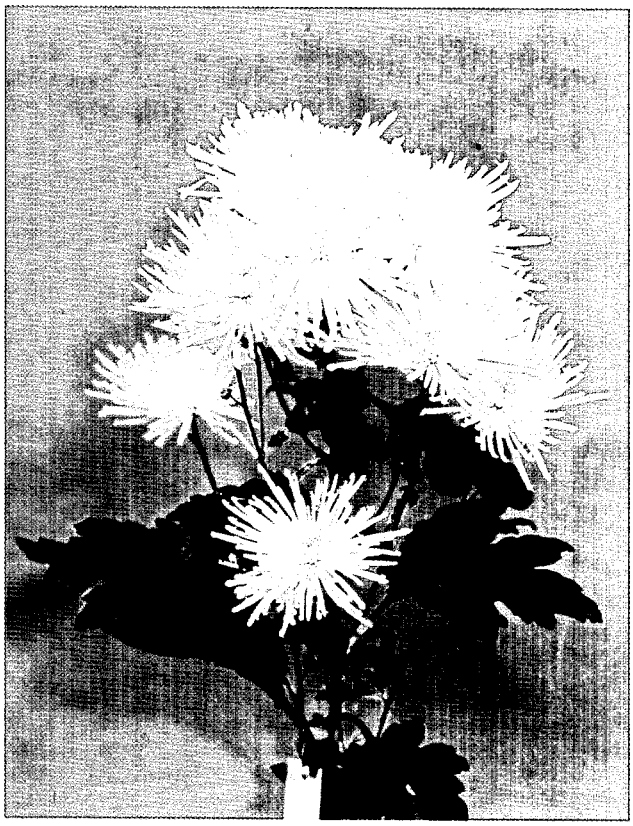

United States Patent Office

Plant Pat. 3,449
Patented Jan. 22, 1974

3,449
CHRYSANTHEMUM PLANT

Hubert Brandkamp, In der Flora 6, Anholt, Westphalia, Germany, and Hermann Vogel, Via delle Grugnole, Tre Cancelli, Nettuno, Italy Filed Jan. 17, 1972, Ser. No. 218,369
Int. Cl. A01h 5/00
U.S. Cl. Plt.—77 1 Claim This invention relates to a new and distinct variety of *Chrysanthemum morifolium* Bailey (spray type) hereinafter referred to as White Snowstar. White Snowstar is a sport from the variety White Spider found in autumn 1967 by us in cultivated ground at Piani di Camporosso, Imperia, Italy. The variety White Spider, an unpatented variety, was originated by Edwin C. Price at Fremont, Calif., U.S.A.

The variety White Spider resulted from an extensive breeding program with the object of producing improved year round sprays for year round chrysanthemum production programs with improved uniformity and response over existing varieties, with particular emphasis on winter production. White Spider fulfilled the need for a new white spray of the spider class. This sport hereinafter referred to as White Snowstar is distinguished from White Spider by its clearly tube-formed petals.

The following unique combination of characteristics distinguish White Snowstar from White Spider, the most similar white year round spider grown in Germany of which we are aware:

(1) It is more responsive all year round, with the response time of ten weeks being always the same. It is less vegetative.
(2) Single flower size is slightly smaller.
(3) The petals are of tube-shape, have blunt ends and do not interfere with each other at their ends.
(4) The color of the center of the bloom is fresher, more of a green-yellow color.

Asexual reproduction of this new variety as performed at Hubert Brandkamp, Jungpflanzen-Gartnereien in Anholt, Westfalen, Germany, by rooting vegetative shoots, shows that the above characteristics are fixed and come true to type and are transmitted through succeeding generations.

The accompanying drawing shows a typical flower of new variety depicted in color as nearly true as it is reasonably possible to make same in a color illustration of this character.

The following is a detailed description of the new variety White Snowstar with color terminology in accordance with the Royal Horticultural Society Color Chart (RHS).

Genus: Chrysanthemum
Species: *Morifolium* Bailey
Type: Spray
Class: Spider
Breeding: Sport from White Spider found at Piani di Camporosso, Imperia, Italy, in autumn 1967. White Spider was originated by Mr. Edwin C. Price in Fremont, Calif., U.S.A.
Propagation: Holds its distinguishing characteristics through succeeding propagations by rooting vegetative shoots.
Flower: 6 to 12 flowers after removal of the center bud.
Bloom size: Average diameter 7 cms. when fully open.
Petalage: 60 to 80 fully developed petals, furthermore the same number of petals developed half and quarter of the normal size in the center of the bloom. Several rings of petals overlapping each other.
Form: Spider.
Petals: Tube-shaped, blunt, detached, strong.
Pedicels: Medium texture, 6 to 12 cms. long.
Color of open bloom:
- Inner face of fully expanded petal, except at petal bottom, RHS 155 D.
- Outer face of fully expanded petal, except at petal bottom, RHS 155 D.
- Inner face of fully expanded petal bottom, RHS 1 B.
- Outer face of fully expanded petal, bottom, RHS 1 B.
- Inner face of young petals, RHS 150 D.
- Outer face of young petals, RHS 150 D.

Response group: 10 weeks.
Temperature tolerance: 59–64.4° F. at night.
Plant: Wiry, upright habit of growth.
Foliage:
- Good quality.
- Average internode length, 7 to 9 cms. Color, RHS 137 B, strong texture.

Stem: Medium thickness and wiry.
Color of stem at flowering: RHS 146 C.

We claim:

1. A new and distinct variety of *Chrysanthemum morifolium* Bailey, substantially as herein shown and described, characterized particularly as to novelty by the unique combination of a wiry, upright plant with spider-flowers having from 60 to 80 fully expanded petals of tube-shape, which are blunt at their ends, an exact response time of 10 weeks over the year.

No references cited.

ROBERT E. BAGWILL, Primary Examiner